United States Patent [19]

Weber

[11] Patent Number: 5,136,041

[45] Date of Patent: Aug. 4, 1992

[54] SYNTHESIS OF 7-AMINO-4,6-DINITROBENZOFUROXAN

[75] Inventor: James F. Weber, Moorpark, Calif.

[73] Assignee: Rockwell International Corporation, Seal Beach, Calif.

[21] Appl. No.: 701,582

[22] Filed: May 14, 1991

Related U.S. Application Data

[63] Continuation-in-part of Ser. No. 556,054, Jul. 20, 1990, abandoned.

[51] Int. Cl.$^5$ ............................................. C07D 271/12
[52] U.S. Cl. ...................................... 548/126; 564/411
[58] Field of Search .......................................... 548/126

[56] References Cited

U.S. PATENT DOCUMENTS

| H,476 | 6/1988 | Norris | 548/126 |
| 4,529,801 | 7/1985 | Norris | 548/126 |
| 4,754,040 | 6/1988 | Chafin | 548/126 |

FOREIGN PATENT DOCUMENTS 205898  1/1984  German Democratic Rep. ..................... 548/126

Primary Examiner—Robert Gerstl
Attorney, Agent, or Firm—H. Fredrick Hamann; Harry B. Field; David C. Faulkner

[57] ABSTRACT

The compound 7-amino-4,6-dinitrobenzofuroxan is prepared by reacting 2,3,4,6-tetranitroaniline in a solvent with aqueous sodium azide under controlled exotherm conditions.

1 Claim, No Drawings

SYNTHESIS OF 7-AMINO-4,6-DINITROBENZOFUROXAN

This is a continuation-in-part of copending application Ser. No. 07/556,054 filed on Jul. 20, 1990, now abandoned.

BACKGROUND OF THE INVENTION

1. Field of the Invention

This invention relates to the field of explosive compounds. More particularly, this invention relates to an improved method for the preparation of 7-amino-4,6-dinitrobenzofuroxan.

2. Description of Related Art

Energetic materials useful as components in solid propellants and explosives as well as methods for preparing same are well known in the art.

The synthesis and characterization of 7-amino-4,6-dinitrobenzofuroxan has been reported in United States Statutory Invention Registration No. H476 (incorporated by reference) wherein monochloro-4,6-dinitrobenzofuroxan in $CH_2Cl_2$ is stirred under an ammonia atmosphere to precipitate the ammonium salt of 7-amino-4,6-dinitrobenzofuroxan. Treatment with dilute hydrochloric acid yields 7-amino-4,6-dinitrobenzofuroxan.

SUMMARY OF THE INVENTION

This invention provides the compound 7-amino-4,6-dinitrobenzofuroxan, useful in solid propellants and the like.

The method of making the compound comprises the nitration of 3-nitroaniline to produce 2,3,4,6-tetranitroaniline followed by reaction with sodium azide in acetic acid to produce 7-amino-4,6-dinitrobenzofuroxan.

OBJECTS OF THE INVENTION

It is an object of this invention to provide a novel and inherently more stable method for the production of 7-amino-4,6-dinitrobenzofuroxan.

This and other objects of the invention will become more readily apparent from the following detailed description.

DESCRIPTION OF THE PREFERRED EMBODIMENT

This invention discloses a novel method for the preparation of 7-amino-4,6-dinitrobenzofuroxan:

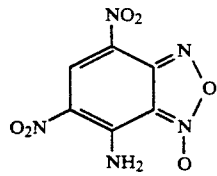

The compound 7-amino-4,6-dinitrobenzofuroxan is an insensitive, thermally stable explosive. The physical and chemical properties of 7-amino-4,6-dinitrobenzofuroxan are presented in Table 1:

TABLE 1

| PROPERTIES | MEASUREMENTS |
|---|---|
| Molecular formula | $C_6H_3N_3O_6$ |
| Molecular weight | 241.12 |
| Density | $1.902 \pm 0.008$ g/cm$_3$ |
| Melting point (DSC. 10°/min) | 270° (decomposition) |
| Oxygen balance (CO) | −10 |
| Percent nitrogen | 29.1 |
| Detonation velocity (calculated) | 7.91 mm/μs |
| Detonation pressure (calculated) | 282 Kbar |
| Impact sensitivity (H$_{30}$)* | 100 cm (TNT ± 75 cm) |
| Heat of formation | +36.79% 0.72 Kcal/mol |

*Bureau of Mines

The production of 7-amino-4,6-dinitrobenzofuroxan is traditionally prepared by nitration of 3-nitroaniline to produce 2,3,4,6-tetranitroaniline followed by reaction with sodium azide in acetic acid to produce 7-amino-4,6-dinitrobenzofuroxan (ADNBF). The existing method utilizes a mixed nitrating acid of 30% oleum and 98% nitric acid for the first step followed by the addition of solid sodium azide. By using anhydrous nitric acid in place of the aforementioned mixed nitric acid complex, and an aqueous solution of sodium azide in the second step, the novel method of the present invention is effected.

Conversion of the 2,3,4,6-tetranitroaniline (TNA) to 7-amino-4,6-dinitrobenzofuroxan (ADNBF), shown in more detail below, is effected by means of displacing a nitro group from TNA with an azide ion. This reaction is carried out in an acetic acid slurry with aqueous sodium azide. The exothermic reaction is easily controlled by means of varying the rate of addition of the sodium azide solution. Excess sodium azide reacts with the side product nitrite ion to form gaseous $N_2O$ and $N_2$. The intermediate 3-azido-2,4,6-trinitroaniline formed is thermally decomposed without isolation to from nitrogen gas and an unstable nitrene which cyclizes with an adjacent nitro group to form the product.

To aid in the understanding of the present method for the production of 7-amino-4,6-dinitrobenzofuroxan, the following example is provided.

EXAMPLE 1

Preparation of 2,3,4,6-Tetranitroaniline (TNA)

A 5,000 ml three-necked round bottom flask with a mechanical stirrer, thermometer, and 250 ml addition funnel was charged with 107 g (0.78 mol) of 3-nitroaniline in 1000 ml of concentrated sulfuric acid and warmed to 60° C. by means of an electric heating mantle. The mantle was removed and 190 ml of anhydrous nitric acid (285 g; 4.52 mol) was added slowly dropwise. The addition rate was adjusted along with an eternal ice water bath to maintain the reaction temperature at 65±3° C. during the addition. After the addition was completed, the mixture was stirred without external heating or cooling for 20 minutes as the reaction temperature subsided slowly. An ice bath was used to then lower the temperature to 40° C. and the thick slurry of product in acid was filtered through a fritted glass Buchner funnel. The flask and filter cake were rinsed with 50% sulfuric acid and then with water, and the yellow-green cake was left to dry on the funnel. The yield was 157 g (74%) as a slightly damp solid which was suitable for the next step without further purification. A small sample was dried to determine the melting point (mp=226° C. with decomposition) and infrared spectrum of this material which were identical with authentic samples.

EXAMPLE 2

Preparation of 7-Amino-4,6-dinitrobenzofuroxan (ADNBF)

In a 5000 ml three-necked round bottom flask equipped with a mechanical stirrer, thermometer, and addition funnel vented to a gas bubbler, the damp filter cake from the TNA preparation (157 g; 0.58 mol max.) was suspended in 700 ml of glacial acetic acid at room temperature. Conversion of the suspended TNA to 3-azido-2,4,6-trinitroaniline was effected by addition of a solution of 76.4 grams (1.18 moles) of sodium azide in 200 ml of water. The temperature was maintained at 20-28° C. by adjusting the addition rate and by use of external cooling. Gas evolution from the reaction of azide ions with the displace nitrate ions to form $N_2O$ and $N_2$ was evident when about one-third of the sodium azide solution had been added and remained smooth until the addition was complete (about 40 minutes). Without isolation of the intermediate 3-azido-2,4,6-trinitroaniline, the reaction flask was heated to 80° C. slowly. Gas evolution from decomposition of the azido group to a nitrene and gaseous nitrogen became vigorous at about 60° C. and ceased after about 30 minutes at 80° C. The nitrene spontaneously cyclizes with the adjacent nitro group to form the product. The reaction was held at 80° C. for a total of 60 minutes and was cooled to room temperature overnight. The product was filtered, washed well with water, and left to air dry on the funnel. The solid product (127 g; ca. 90% yield) was stored damp. A small sample was dried for infrared spectral analysis and melting point (mp=274-275° C., with decomposition) which were identical to those of authentic samples.

The subject invention has been described in detail sufficient to inform one skilled in the art with the method of manufacture with reference to a preferred embodiment thereof. However, it will be understood that variations and modifications can be effected within the spirit and scope of the invention.

What is claimed is:

1. A method for the preparation of 7-amino-4,6-dinitrobenzofuroxan comprising:
   (a) in a suitable reaction vessel forming a mixture of 2,3,4,6-tetranitroaniline and glacial acetic acid;
   (b) admixing aqueous sodium azide with said mixture while controlling exotherm by initially maintaining the reaction temperature at from 20° C. to 28° C. for 30 minutes and then increasing the temperature to 80° C. for 60 minutes; and
   (c) thus reacting said mixture and aqueous sodium azide to yield 7-amino-4,6-dinitrobenzofuroxan.

* * * * *